United States Patent [19]
Tenzer

[11] Patent Number: 5,980,541
[45] Date of Patent: *Nov. 9, 1999

[54] ORAL HYGIENE DEVICE

[76] Inventor: Mihyang Nicole Tenzer, 230 W. 55th St., New York, N.Y. 10019

[ * ] Notice: This patent issued on a continued prosecution application filed under 37 CFR 1.53(d), and is subject to the twenty year patent term provisions of 35 U.S.C. 154(a)(2).

[21] Appl. No.: 09/088,443

[22] Filed: Jun. 1, 1998

Related U.S. Application Data

[62] Division of application No. 08/748,007, Nov. 12, 1996, abandoned.

[51] Int. Cl.$^6$ ................................................. A61B 17/24
[52] U.S. Cl. ................................................. 606/161; 15/111
[58] Field of Search ................................. 606/161, 163, 606/164; 15/111

[56] References Cited

U.S. PATENT DOCUMENTS

| | | | |
|---|---|---|---|
| 1,728,956 | 9/1929 | Darmitzel | 606/161 |
| 2,083,217 | 6/1937 | Brothers et al. | |
| 2,574,654 | 11/1951 | Moore | |
| 2,765,799 | 10/1956 | Ritter | |
| 3,811,447 | 5/1974 | Weber | 128/304 |
| 4,041,564 | 8/1977 | Schlicher | 15/111 |
| 4,455,704 | 6/1984 | Williams | 15/111 |
| 5,005,246 | 4/1991 | Yen-Hui | 15/111 |
| 5,530,981 | 7/1996 | Chen | 15/111 |
| 5,778,475 | 7/1998 | Garcia | 15/111 |
| 5,792,159 | 8/1998 | Amin | 606/161 |

*Primary Examiner*—Michael Buiz
*Assistant Examiner*—Kevin Truong
*Attorney, Agent, or Firm*—Cantor Colburn PC

[57] ABSTRACT

Disclosed is an oral hygiene device, comprising an elongate handle having a bristle end and a scraper end, the bristle end having a plurality of bristles disposed thereon adapted to brushing the user's teeth as in a conventional toothbrush. An arcuate blade member is provided having a concave surface and an opposing convex surface and at least one blade edge disposed at a juncture of the convex and concave surfaces and wherein the curvature of the arcuate blade member is sized, shaped and adapted to scraping the upper surfaces of the human tongue. the arcuate blade member is disposed and attached by support member to the scraper end of the elongate handle such that the concave surface faces the scraper end of the elongate handle. The tongue scraper of the device is used by placing a blade edge upon the convex top surface portion of the human tongue back near the root of the tongue while holding the elongate handle at a downward angle so as to effectively engage the blade edge with the top surface of the tongue and then dragging the blade edge forward and across the convex portion of the tongue, the intermediate portion of the tongue, and the concave forward portion of the tongue, while simultaneously adjusting the angle of the elongate handle upward so as to maintain effective engagement of the blade edge with the top surface of the tongue.

5 Claims, 3 Drawing Sheets

ORAL HYGIENE DEVICE

PRIOR HISTORY

This application is a divisional application under 37 C.F.R. §1.53(b) of U.S. Ser. No. 08/748,007, filed Nov. 12, 1996 now abandoned.

BACKGROUND OF THE INVENTION

This invention relates to oral hygiene devices, more specifically for devices for scraping or cleaning the tongue in combination with a toothbrush.

DESCRIPTION OF THE RELATED ART

U.S. Pat. No. 5,530,981, "Toothbrush Having a Tongue Scraper Disposed Therein," issued Jul. 2, 1996, to Chen, discloses a toothbrush having a scraper disposed therein includes a handle and a bristle portion which has a barrel connected therewith and is pivotally engaged to the handle with a cylinder disposed to the barrel pivotally engaged between two ears extending from an end of the handle, the handle having a groove defined in a side thereof for the scraper to be inserted therein, each of the ears having a first recess defined therein and the cylinder having a plurality of short grooves defined in both ends thereof, the scraper having a first end and having two parts extending therefrom for insertion into said short grooves, a hook portion formed to one of the parts laterally and engaged with the first recess of the ear, the scraper having a T-shaped plate slidably received in the groove of the handle.

U.S. Pat. No. 5,005,246, "Replaceable Tooth Brush with Tongue Scaler," issued Apr. 9, 1991, to Yen-Hui, discloses a toothbrush provided with a replaceable bristle holder that is detachably receivable within a trough formed in the brush head and secured in position by a head cover, with the cover and the trough being configured for engaging corresponding portions of the bristle holder. A tongue scaler is slidably supported within the handle portion of the brush and a corresponding handle cover provided with a track engageable by a tenon formed on an end of the scaler to permit the scaler to be extended into a position of use or retracted into a position of storage with respect to the handle.

U.S. Pat. No. 4,455,704, "Toothbrush and Tongue Cleaner," issued Jun. 26, 1984, to Williams discloses a conventional toothbrush combined with a tongue cleaner as a single instrument, adapted to provide cooperative improved personal hygiene. A toothbrush has a handle integrally extending coextensively from the conventional toothbrush bristle segment, the opposed handle terminating in an integral arcuate structure curve at the opposed handle terminus. The arcuate scraper member can also be formed to be removable from the toothbrush handle. The terminal arcuate scraper structure is provided to the toothbrush user to scrape the user's top tongue surface, removing food particles and the like, which can decay and provide offensive odors and tooth decay agents. The toothbrush user can wash the user's teeth with conventional tooth cleaner material in the conventional manner, then reverse the tooth brush in their hand and scrape the top surface of the user's tongue, further removing food particles and the like. The toothbrush and scraper combination is then washed for re-use, if required. The invention provides single instrumentation for the oral cleaning process.

U.S. Pat. No. 4,041,564, "Combination Scraper and Brush with Extensible Handle," issued Aug. 16, 1977, to Schlicher, discloses an extensible scraping and brushing tool for use in removing ice and snow from vehicle windows or the like has an elongate handle provided with a scraper member at one end and has a brush assembly that is telescopically received in the handle. The brush assembly is nested in the handle when the tool is to be used as a scraper or as a brush of a relatively short length or, the brush assembly may be extended from such a first position to a second position in which the brush assembly extends beyond the handle in order that the tool may be used as a brush having an extended reach. Guide structure for reciprocably shifting the brush assembly and retaining the same in connection with the handle is formed integrally as a part of the handle and brush assembly and is of a configuration providing a relatively high degree of rigidity at the point of connection between the two when the tool is in its extended condition. The brush assembly and the handle are so constructed that the complete tool may be assembled by press-fitting the components together, eliminating the need for fasteners or other special assembly procedures.

U.S. Pat. No. 3,811,447, "Oral Hygiene Appliance," issued May 21, 1974, to Weber, discloses an oral hygiene appliance for removing plaque from interior surfaces of the mouth not adequately cleaned by conventional toothbrushing. The device comprises two V-shaped jackets pivotally joined at one end by a pin. A flat elongate tongue scraper blade is held by the pin at one end within a first jacket. The blade is angularly moveable between a storage position within the jacket and a use position exterior to the jacket. A flat spool swivels into and out of the other jacket in a similar manner.

U.S. Pat. No. 2,765,799, "Combined Retractable Scaler and Toothbrush," issued Jan. 17, 1955, to Ritter, relates to a combined toothbrush and tooth scaler wherein the scaler is springloaded inside the handle of the toothbrush and pops out when a butto9n on the side of the toothbrush handle is depressed. The scaler has an arcuate hook used to scrape tarter out from between teeth.

U.S. Pat. No. 2,574,654, "Tongue Cleaner," issued Nov. 13, 1951, to Moore, relates to a tongue scraper comprising a handle, channel-shaped fingers providing clamping means for detachably securing said scraper to said handle, a blade on said tongue scraper, a trapezoidal plate joining said blade to said fingers, said plate having depending flanged edges reinforcing said plate.

U.S. Pat. No. 2,083,217, "Prophylactic Device for the Oral Cavity," issued Jun. 8, 1937, to Brothers et al., relates to a combination of an elongated stock provided with a plurality of hard and tight bristle knots arranged in a single row and spaced apart, and said knots being provided in their free ends with centrally aligned channels extending longitudinally of the stock and medially across the free end of the knots.

U.S. Pat. No. 1,728,956, "Combination Toothbrush and Tongue Scraper," issued Sep. 24, 1929, to Darmitzel, relates to a tongue scraper comprising an elongated handle increasing gradually in width toward one end, a flat blade of substantially rectangular shape formed on the larger end of the handle and disposed at right angles with respect thereto, said blade being joined at its upper central portion to the larger end of the handle, the upper corners of the blade being rounded, said blade tapering gradually toward its lower edge.

BRIEF SUMMARY OF THE INVENTION

A toothbrush is integrally combined with a tongue scraper. The invention comprises an elongate handle having conventional toothbrush bristles disposed at a proximate end and the tongue scraper integrally mounted on a distal end. The tongue scraper comprises an arcuate blade, preferably two-sided, such that the arc of the blade is disposed in a plane preferably congruent to that of the handle, while the edge or edges of the blade are perpendicular to the plane containing said arc. The curvature of the arcuate blade is such that the focus of curvature is disposed between the blade and the proximate end of said handle, that is to say that the concave side of the arcuate blade faces the handle and the convex side of the arcuate blade faces away from the handle. The curvature of the arcuate blade is adaptively sized and shaped to scrape the top of the user's tongue. An aperture is defined between the blade edges and the elongate handle so as to accommodate the curvature of the tongue when the blade is pressed thereon.

Also disclosed is a method for using the apparatus of the present invention wherein the user places the blade on the convex surface of the tongue located toward the throat near the uvula with the elongate handle tilted downward so as to conform the inside concave side of the arcuate blade to the shape of the tongue. The user then drags the blade forward, lifting the handle simultaneously, so that the convex side of the arcuate blade conforms to the concave shape of the tip of the tongue.

The scraping of the tongue removes particles and residue that cause bad breath and promote tooth decay.

DETAILED DESCRIPTION OF THE INVENTION

Disclosed is an oral hygiene device, comprising an elongate handle having a bristle end and a scraper end, said bristle end having a plurality of bristles disposed thereon adapted to brushing the user's teeth as in a conventional toothbrush. An arcuate blade member is provided having a concave surface and an opposing convex surface and at least one blade edge disposed at a juncture of said convex and concave surfaces and wherein the curvature of said arcuate blade member is sized, shaped and adapted to scraping the upper surface of the human tongue. the arcuate blade member is disposed and attached by support means to said scraper end of said elongate handle such that said concave surface faces said scraper end of said elongate handle.

The tongue scraper of the device is used by placing a blade edge upon the convex top surface portion of the human tongue back near the root of the tongue while holding said elongate handle at a downward angle so as to effectively engage said blade edge with the top surface of the tongue and then dragging said blade edge forward and across the convex portion of the tongue, the intermediate portion of the tongue, and the concave forward portion of the tongue, while simultaneously adjusting the angle of said elongate handle upward so as to maintain effective engagement of said blade edge with the top surface of the tongue.

Figure 1:
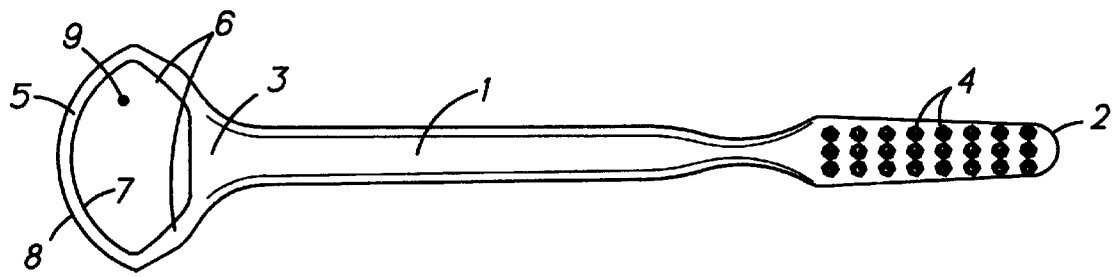
FIG. 1 is a top plan view of an embodiment of the invention.

Referring to FIG. 1, there is provided an elongate handle 1 having a bristle end 2 and a scraper end 3. Bristles 4 are disposed on the bristle end so as to provide the functionality of a conventional toothbrush. Provided is an arcuate blade member 5 disposed and attached to the scraper end of the handle by support means 6, which in this figure are simply a pair of support beams. The arcuate member has a concave 7 and a convex 8 surface and is supported by the support means such that the concave surface faces the scraper end of the elongate handle. The support means and arcuate blade member together define an aperture 9 between the arcuate blade member and the scraper end of the toothbrush handle.

Figure 2:
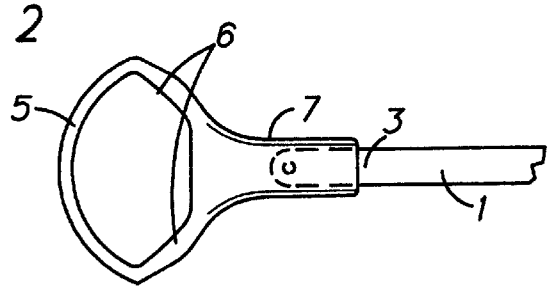
FIG. 2 is a top plan view of a removable scraper embodiment of the invention.

FIG. 2 depicts a removable embodiment of the invention wherein the scraper end 3 of the handle 1 is removably attached to means for supporting the arcuate blade member 5 and support means 6. In this embodiment, the means of support are attached to a simple socket 7 that is adapted to receive the scraper end 3 of a toothbrush.

Figure 3:
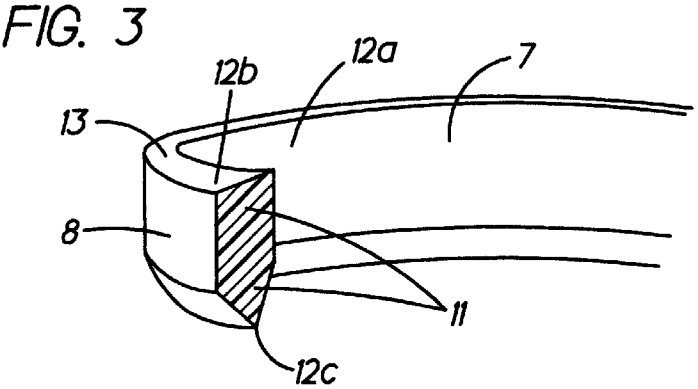
FIG. 3 is a side cross-sectional view of the scraper blade of the invention.

Referring to FIG. 3, it can be seen that the arcuate blade member, having a convex 8 and concave 7 surface, will preferably have at least one, and preferably two, blade edges 11 disposed at the junctures of said concave and convex surfaces. Note that for the purposes of this disclosure the term "blade edge" is not limited to a single scraping edge 12. Note that the upper blade edge in the drawing has a lateral surface 13 interposed between the concave and convex surfaces that define two scraping edges, an inner scraping edge 12a and an outer scraping edge 12b—which will be referred to herein as a "right-angle" blade edge—while the lower blade edge is simply sharpened to a single scraping edge 12c, herein referred to as an "acute" blade edge. The figure depicts a preferred embodiment wherein both types, right-angle and acute, are provided on a single arcuate blade member so as to provide a choice of scraping surfaces to the user. The distance between the blade edges will generally be about ⅛ to ⅜ of an inch.

Figure 4:
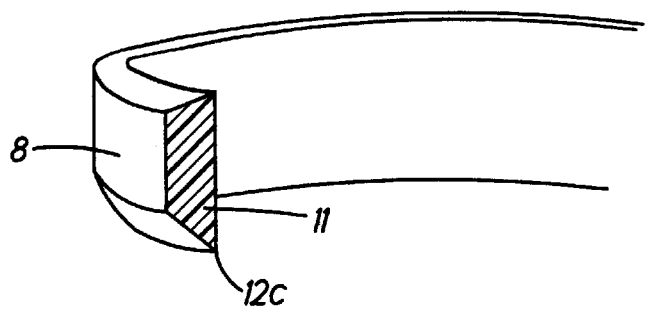
FIG. 4 is side cross-sectional view of another embodiment of the scraper blade of the invention.

FIG. 4 depicts an alternative embodiment of the acute blade edge 11 in which the single scraping edge 12c is formed by beveling the outer convex surface 8 only.

Figure 7:
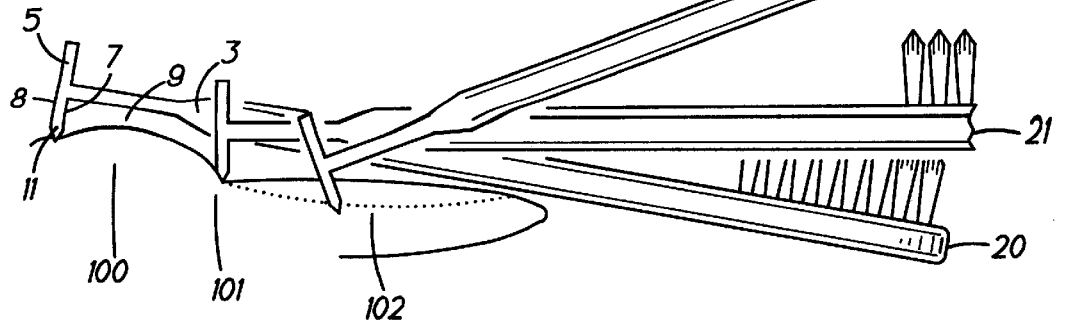
FIG. 7 is a side cross-sectional view of the process of the invention using the embodiment of the device depicted in FIGS. 4 and 5.

The curvature of the arcuate blade member must be adapted to effectively engage the human tongue. The invention is novel in that is anticipates a realistic view of the geography of the human tongue. In a relaxed state, the upper surface of the tongue is basically flat. However, when a foreign object, such as a tongue scraper or tongue depressor, is pressed down upon the tongue, the tongue will usually tense and resile into the configuration depicted in FIG. 7. The reader may verify this in a mirror. In the tensed configuration, the upper surface of the tongue may be subdivided into three portions, a rearward upwardly convex portion 100, a middling flat or transition portion 101, and a forward concave portion 102. The scraper assembly of the present invention is adapted to scrape all three tongue portions.

Referring again to FIG. 7, to effectively engage the arcuate blade member with the tongue, the user simply tilts the elongate handle into a downward first position 20 so as to present the concave surface 7 of the arcuate blade member 5 to the convex portion 100 of the tongue. The user then drags the device forward, tilting the elongate handle upward and through positions 21 and 22 as he goes, such that neither concave 7 nor convex 8 surface of the arcuate blade member is presented while scraping the flat intermediate portion 101 of the tongue, and wherein the convex surface 8 is presented to the tongue while scraping the forward concave portion 102 of the tongue. Examining the first position 20, it is now apparent why an aperture 9 between the blade edge 11 and the scraper end 3 of the device is preferred.

In adapting the curvature of the arcuate blade member to effectively engage the curvatures of the human tongue, the curvature will generally correspond to a circular arc having a radius of from about 1 inch to about 3 inches, more preferably of from about 1.5 inches to about 2.5 inches, or about 2 inches. The width of the arc is preferably enough to cover the width of the tongue, namely about 1.5 inches.

Figure 5:
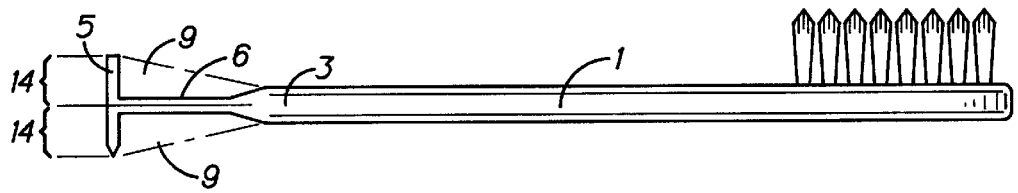
FIG. 5 is a side cross-sectional view of another embodiment of the invention.
Figure 6:
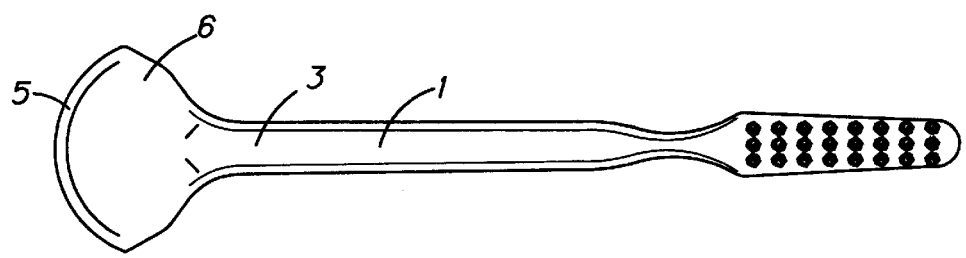
FIG. 6 is a top plane view of the embodiment of FIG. 5.

FIGS. 5 and 6 depict an alternative embodiment of the invention than that depicted in FIG. 1. Here, the support means 6 is a fan-shaped solid member depending from the scraper end 3 of the elongate handle 1 directly to the inside concave surface of the arcuate scraper member 5. This has the advantage of superior structural strength over the embodiment of FIG. 1. However, in this embodiment, it is necessary to dispose the blade edges 11 a further distance 14 from the central axis of the elongate handle so as to create a "virtual" aperture 9 between the blade edges and the scraper end. In this embodiment it is preferred that the distance 14 be at least 3/16 of an inch, preferably about 1/4 inch. Just as shown in FIG. 2, this embodiment may also be removably mounted.

Figure 8:
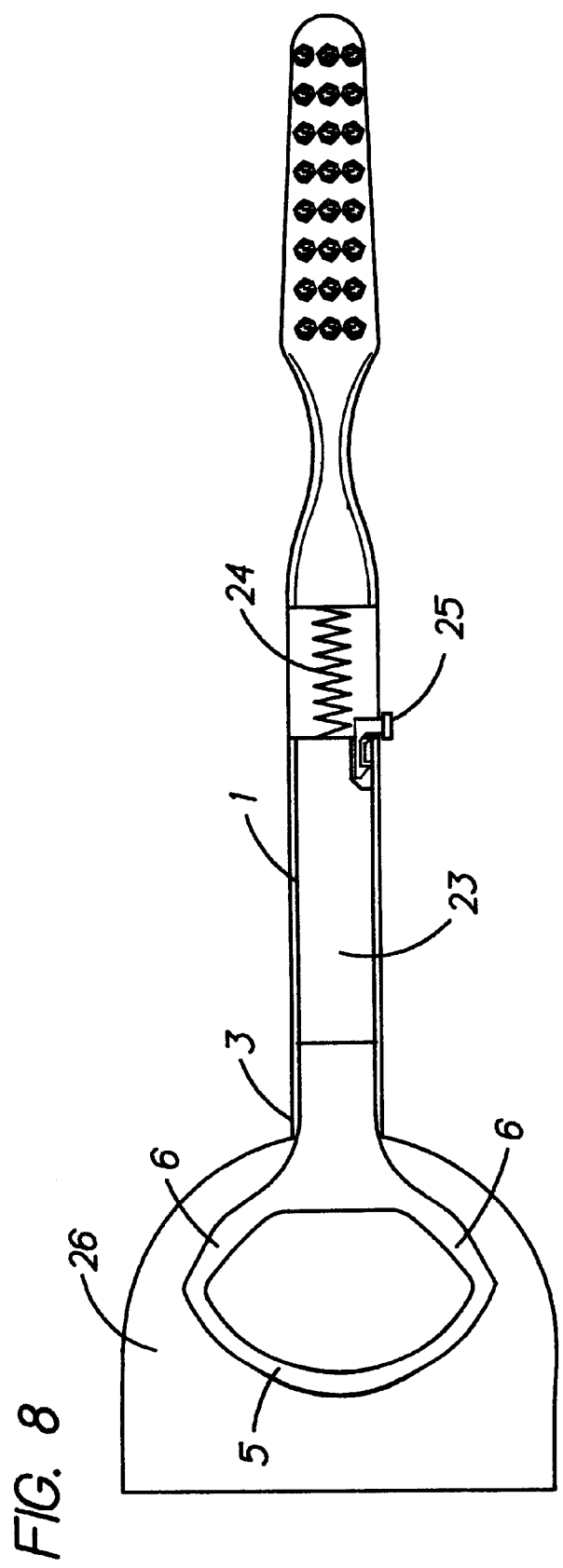
FIG. 8 is a top plan view of a spring-loaded embodiment of the invention.

FIG. 8 depicts a springloaded embodiment of the invention wherein the scraper blade 5 is connected by support means to a slide shaft 23 slideably mounted within the handle 1. Spring means 24 place tension upon the slide shaft such as to push the slide shaft out of the handle. Latch means 25 are provided effective in retaining the slide shaft in a first retracted position within the handle against the force of the spring means. The latch means is preferably in the form of a switch or button so as to allow the user to easily release the slide shaft with his thumb. When latched into the handle in the first retracted position, the scraper blade 5 is concealed within a cowling 26 attached to the scraper end 3 of the device. When released, the scraper blade pops out of the cowling into a second extended position (not shown) and is available for use as described above.

Changes and modifications can be made by those skilled in the art to the embodiments as disclosed herein and such examples, illustrations, and theories are for explanatory purposes and are not intended to limit the scope of the claims.

I claim:

1. An oral hygiene device, comprising:

an elongate handle having a bristle end and a scraper end, said bristle end having a plurality of bristles disposed thereon adapted to brushing the user's teeth;

an arcuate blade member having a concave surface and an opposing convex surface;

at least one blade edge disposed at a juncture of said convex and concave surfaces wherein the curvature of said arcuate blade member is sized, shaped and adapted to scraping upper convex, concave, and flat surfaces of the human tongue;

said arcuate blade member disposed and attached by support means to said scraper end of said elongate handle such that said concave surface faces said scraper end of said elongate handle;

said support means comprises a generally fan-shaped solid member depending from said scraper end of said elongate handle to said concave surface of said arcuate blade member; and said at least one blade edge are disposed a distance away from said fan-shaped solid member so as to form an unobstructed space between said blade edges and said scraper end.

2. The oral hygiene device of claim 1 wherein:

said at least one blade edge comprises two scraper edges.

3. The oral hygiene device of claim 1 wherein:

said at least one blade edge is beveled to a single scraper edge.

4. The oral hygiene device of claim 1 wherein:

said arcuate blade member defines a substantially circular arc segment corresponding to a circle having a radius of from 1 inch to 3 inches.

5. A method of scraping the human tongue, comprising:

obtaining the oral hygiene device of claim 1;

placing a blade edge upon the convex top surface portion of the human tongue back near the root of the tongue while holding said elongate handle at a downward angle so as to effectively engage said blade edge with the top surface of the tongue;

dragging said blade edge forward and across the convex portion of the tongue, the intermediate portion of the tongue, and the concave forward portion of the tongue;

simultaneously adjusting the angle of said elongate handle upward so as to maintain effective engagement of said blade edge with the top surface of the tongue.

* * * * *